United States Patent
Danby et al.

(10) Patent No.: US 6,677,753 B1
(45) Date of Patent: Jan. 13, 2004

(54) STAND-UP MRI APPARATUS

(75) Inventors: Gordon T. Danby, Wading River, NY (US); Jevan Damadian, East Northport, NY (US); John Linardos, Smithtown, NY (US); Raymond V. Damadian, Woodbury, NY (US); Hank Hsieh, Berkeley, CA (US); William H. Wahl, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 372 days.

(21) Appl. No.: 09/718,946

(22) Filed: Nov. 22, 2000

Related U.S. Application Data

(60) Provisional application No. 60/167,460, filed on Nov. 24, 1999.

(51) Int. Cl.⁷ .................................................. G01V 3/00
(52) U.S. Cl. ...................................... 324/318; 324/319
(58) Field of Search ........................ 324/319, 318, 324/320, 300, 306, 307, 309; 5/601

(56) References Cited

U.S. PATENT DOCUMENTS

| | | | |
|---|---|---|---|
| 4,534,358 A | 8/1985 | Young .......................... 128/653 |
| 4,629,989 A | 12/1986 | Riehl et al. ................... 324/318 |
| 4,829,252 A | 5/1989 | Kaufman ..................... 324/309 |
| 4,924,198 A | 5/1990 | Laskaris ....................... 335/216 |
| 4,968,937 A | 11/1990 | Akgun ......................... 324/318 |
| 4,985,678 A | 1/1991 | Gangarosa et al. .......... 324/318 |
| 5,008,624 A | 4/1991 | Yoshida ....................... 324/318 |
| 5,065,761 A | 11/1991 | Pell ........................ 128/660.03 |
| 5,153,546 A | 10/1992 | Laskaris ....................... 335/216 |
| 5,162,768 A | 11/1992 | McDougall et al. ......... 335/296 |
| 5,197,474 A | 3/1993 | Englund et al. .......... 128/653.3 |
| 5,305,749 A | 4/1994 | Li et al. ................... 128/653.2 |
| 5,436,607 A | 7/1995 | Chari et al. .................. 335/216 |
| 5,592,090 A | 1/1997 | Pissanetzky ................. 324/319 |
| 5,606,970 A | 3/1997 | Damadian ................ 128/653.2 |
| 5,735,278 A | 4/1998 | Hoult et al. .............. 128/653.2 |
| 5,983,424 A * | 11/1999 | Naslund ......................... 5/601 |
| 6,023,165 A | 2/2000 | Damadian et al. ........... 324/318 |
| 6,246,239 B1 * | 6/2001 | Krogmann et al. .......... 324/318 |
| 6,335,623 B1 * | 1/2002 | Damadian et al. ........... 324/320 |
| 6,414,490 B1 * | 7/2002 | Damadian et al. ........... 324/319 |

OTHER PUBLICATIONS

U.S. patent application 09/789,460.

* cited by examiner

*Primary Examiner*—Edward Lefkowitz
*Assistant Examiner*—Brij B. Shrivastav
(74) *Attorney, Agent, or Firm*—Lerner, David, Littenberg, Krumholz & Mentlik, LLP

(57) ABSTRACT

A magnet for magnetic resonance imaging has a box-like ferromagnetic frame with vertical side walls, poles connected to the side walls and top and bottom walls forming flux return structures between the side walls. The frame has open front and rear sides defining patient entry openings, and has top and bottom openings in the top and bottom walls. A patient can be positioned in a vertical, horizontal or intermediate orientation within the frame. When the patient is in the vertical orientation, the patient can be raised or lowered so that parts of the patient's body protrude into the top or bottom openings, so as to align any part of the patient's body with the poles. The apparatus allows imaging of any part of the anatomy while the patient is in a standing position.

31 Claims, 8 Drawing Sheets

STAND-UP MRI APPARATUS

CROSS-REFERENCE TO RELATED APPLICATIONS

The present application claims the benefit of U.S. Provisional Application No. 60/167,460, filed Nov. 24, 1999, the entire disclosure of which is hereby incorporated by reference herein.

BACKGROUND OF THE INVENTION

The present invention relates generally to a magnetic resonance imaging ("MRI").

Magnetic resonance imaging is widely used in medicine for providing images of internal structures within the body of a patient. MRI offers numerous advantages over other imaging techniques such as x-ray and computerized axial tomography (CAT) imaging. MRI does not expose the patient to ioning radiation and can capture images of tissues which are not readily shown by other techniques.

To produce an MRI image, a strong, uniform magnetic field is applied to the region of the patient to be imaged. Radio frequency ("RF") energy is applied to this region of the patient by a transmitter and antenna. The RF energy excites atomic nuclei within the patient's tissues. The excited nuclei spin at a rate dependent upon the magnetic field. As they spin, they emit faint RF signals, referred to herein as magnetic resonance signals. By applying small magnetic field gradients so that the magnitude of the magnetic field varies with location within the patient's body, the magnetic resonance phenomenon can be limited to only a particular region or "slice" of the patient's body, so that all of the magnetic resonance signals come from that slice. Moreover, by applying additional magnetic field gradients, the frequency and phase of the magnetic resonance signals from different locations within the slice can be made to vary in a predictable manner depending upon the position within the slice. Thus, it is possible to distinguish between signals from different parts of a slice.

If this process is repeated numerous times using different gradients, it is possible to derive a map showing the intensity or other characteristics of magnetic resonance signals from particular locations within the patient's body. Because these characteristics vary with the concentration of different chemical substances and other chemical characteristics of the tissues, different tissues provide different magnetic resonance signal characteristics. When the map of magnetic resonance signal characteristics versus location is displayed in a visual format, such as on a computer screen or printed image, the map forms a picture of the structures within the patient's body, with different tissues having different intensities or colors. The magnets used in MRI imaging must provide a magnetic field which is strong and uniform. Preferably, the magnet of the MRI imaging apparatus has a patient-receiving space capable of receiving the torso of a normal human being, and provides a field strength of at least 1 kilogauss and preferably at least about 3 kilogauss or more. This field desirably is uniform to within about 1 part in $10^7$ or better in an imaging volume at least about 25 cm in diameter in the patient-receiving space.

The required fields can be generated by a so-called air-core solenoidal superconducting magnet. These magnets have coils positioned along a horizontal axis and a tubular central bore inside the coils. The patient is placed inside this tubular bore while he or she is being imaged. Although magnets of this type can provide acceptable images, they subject to the patient to an intensely claustrophobic experience for the duration of the imaging procedure. Moreover, these magnets inherently require that the imaging procedure be conducted with the patient in a horizontal orientation, lying prone or supine on a bed.

Other magnets utilize ferromagnetic frames. These frames typically include a bottom pole support plate, a set of columns extending upward from the bottom pole support plate and a top pole support plate supported by the columns. Ferromagnetic poles extend upwardly from the bottom pole support plate and downwardly from the top pole support plate so that the poles define the patient-receiving space of the magnet between them. A source of magnetic flux such as superconducting or resistive electromagnet coils encircling the poles or a mass of permanent magnet material is associated with the frame. Magnetic flux passes into the patient-receiving space through the face of one pole and passes out of the patient-receiving space through the face of the opposite pole. The flux returns through the pole support plates and columns.

Certain ferromagnetic frame magnets provide numerous advantages including high field strength and good field uniformity. However, these magnets typically also require that the patient be in a horizontal position.

As disclosed in certain embodiments of U.S. Pat. No. 6,023,165, the disclosure of which is hereby incorporated by reference herein, and in co-pending commonly assigned U.S. patent application Ser. No. 08/978,084, the disclosure of which is also incorporated by reference herein, it is sometimes desirable to acquire an MRI image while the patient is in a vertical or nearly vertical position, such as a standing position. Other positions intermediate between a vertical and horizontal position as, for example, a Trendlenberg or reverse Trendlenberg position can be employed. Certain magnets disclosed in the '165 patent and in the 978,084 application have ferromagnetic frames with horizontal pole axes and can accommodate a patient in a horizontal, vertical or intermediate position.

However, despite these advances in the art, still further improvement would be desirable. In particular, it would be desirable to provide magnets which combine ease of patient entry and egress and a relatively non-claustrophobic patient experience. It would also be desirable to provide apparatus which combines these features with the ability to image essentially any location in the body, including the head and feet, while the patient is in either a vertical or horizontal position. It would be desirable to provide these features in a magnet which can be built at reasonable cost and which provides good field characteristics. Further, it would be desirable to provide these features in a magnet which can be mounted so as to isolate the magnet from mechanical vibrations, for example, vibrations of the earth caused by vehicular traffic. These goals, taken together, present a significant challenge.

SUMMARY OF THE INVENTION

One aspect of the invention provides MRI apparatus. The apparatus according to this aspect of the invention desirably includes a magnet frame having two vertically-extending side walls and a pair of ferromagnetic poles projecting inwardly along a polar axis from each said side wall towards the other said side wall. The apparatus also includes a top flux return structure extending between the side walls above the poles and a bottom flux return structure extending between said side walls the poles. The frame defines a patient receiving space within said interior space between the poles. Patient entry openings defined by the side walls and flux return structure desirably allow patient entry and exit. A floor structure preferably is provided in proximity to the bottom flux return structure so that a patient may enter said patient-receiving space by moving across the floor structure and entering into the frame on or above the bottom flux return structure. A source of magnetic flux such as electromagnet coils or permanent magnets provides magnetic flux in the patient-receiving space through said poles. The remainder of the frame provides a return path for the flux. The top flux return structure, bottom flux return structure or, preferably, both flux return structures, have openings aligned with said patient-receiving space. These openings preferably are of sufficient size to accommodate at least a part of the patient. An elevator may be provided for raising and lowering a patient relative to said frame. Thus, while a patient is disposed in the interior of the frame, the patient can be raised or lowered so that a part of the patient, such as the head or feet, protrudes into one of the openings in a flux return structure and another part of the patient is disposed in the patient receiving space, in alignment with the poles. Thus, essentially any part of the patient can be imaged while the patient is in a vertical orientation, such as in a standing posture.

In a particularly preferred arrangement, the apparatus includes a carriage, the elevator being mounted to the carriage for movement with the carriage into and out of the frame. The apparatus desirably further includes a patient support mounted to the elevator, the elevator being operative to raise and lower the patient support relative to the carriage and hence relative to the magnet frame. Most preferably, the elevator and the patient support can be pivoted relative to the carriage through a range of positions including a horizontal position and a vertical position, so that the patient can be positioned in essentially any orientation.

The ferromagnetic frame, with substantially symmetrical flux return elements, provides excellent field characteristics, but nonetheless allows patient positioning as discussed above. The frame can be supported by vibration isolators such as inflatable bladders.

A further aspect of the invention provides methods of magnetic resonance imaging. A method according to this aspect of the invention desirably includes the steps of positioning a patient within a magnet having a frame as discussed above. The positioning step desirably includes advancing the patient into the frame through an entry opening defined by the side walls and said flux return structures so that the patient passes into the frame above the bottom flux return structure and below the top flux return structure. The method further includes the step of conducting magnetic resonance imaging of the patient using the magnet. The step of positioning the patient may include orienting the patient substantially vertically within the frame and raising or lowering the patient relative to the frame so that one portion of the patient extends into an opening in one of said flux return structures and another portion of the patient is disposed in the patient-receiving space for imaging.

For example, the step of positioning the patient desirably includes advancing the patient into the frame on a support carried by a carriage, and the step of raising or lowering the patient preferably includes raising or lowering the support relative to the carriage. The step of advancing the patient into the frame may be performed while the patient is in a substantially horizontal orientation, in which case the step of positioning the patient further includes pivoting the support to bring the patient to the substantially vertical orientation while the patient is at least partially disposed within the frame of the magnet.

Methods according to this aspect of the invention provide extraordinary versatility in imaging.

These and other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 4:
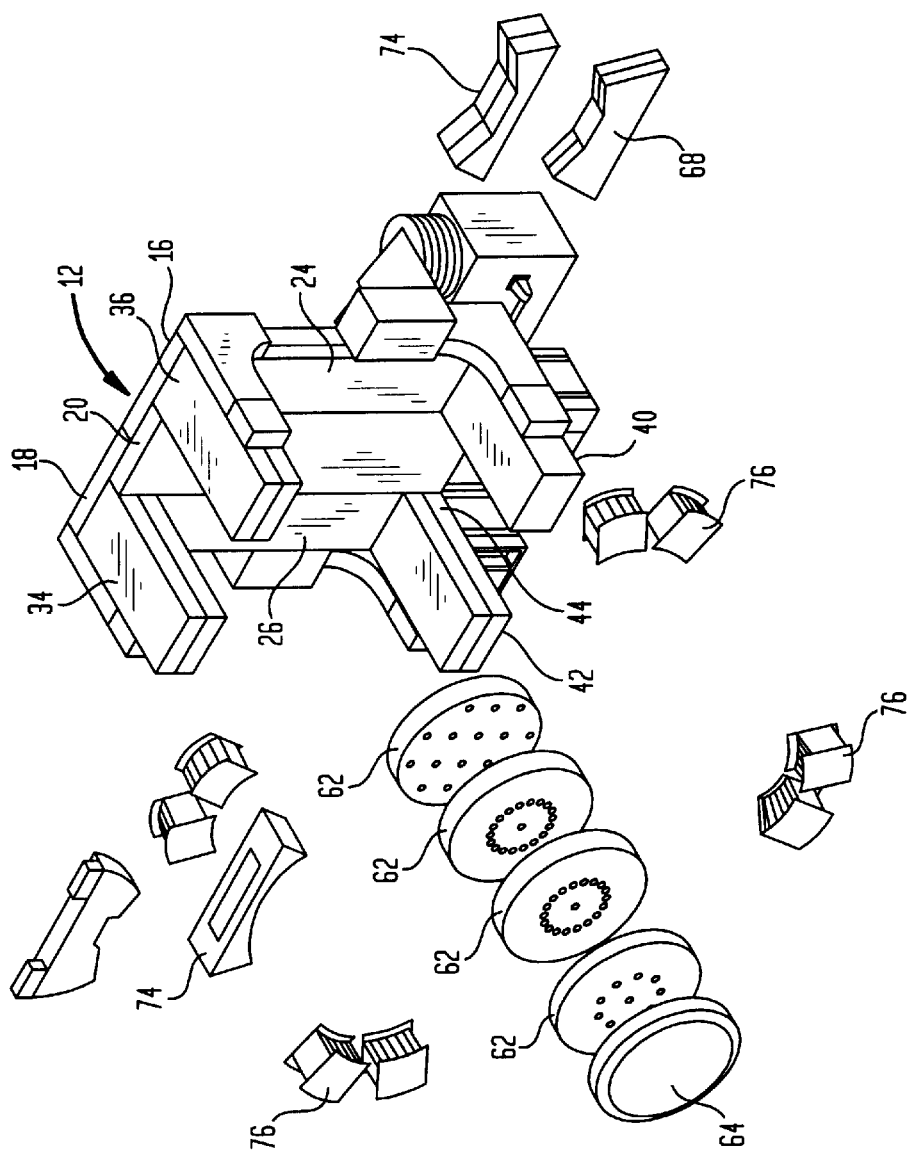
FIG. 4 is a partial exploded view of the structure depicted in FIGS. 1–3.

Magnetic resonance imaging apparatus in accordance with one embodiment of the invention includes a ferromagnetic frame 10. Frame 10 includes a right side wall or pole support plate 12 and a left side wall or pole support plate 14. These side walls extend vertically. As best seen in FIG. 4, first side wall 12 is made up of two layers of ferromagnetic slabs. The outermost layer includes slabs 16 and 18 disposed side by side and extending the full height of the frame. The inner layer includes a further full height slab 20 and a pair of partial height slabs 24 and 26 extending alongside of slab 20. The left side wall 14 has a similar structure.

Figure 1:
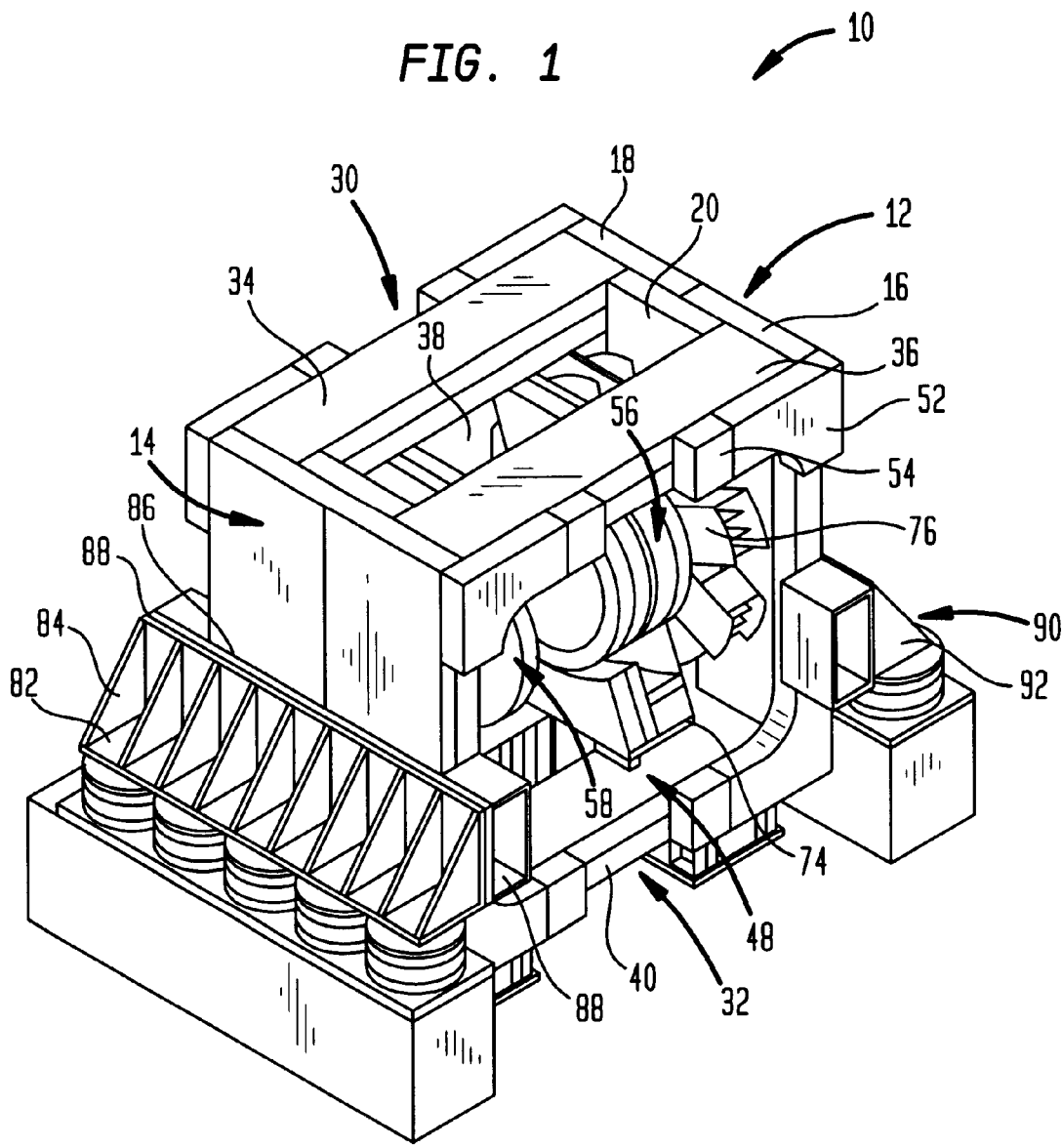
FIG. 1 is a perspective view of a magnet structure in accordance with one embodiment of the invention with certain portions removed for clarity of illustration.

Frame 10 also includes a top flux return structure 30 and a bottom flux return structure 32 extending between side walls 12 and 14 at the top and bottom thereof. The top flux return structure 30 includes two columns 34 and 36. Each such column is formed from two superposed slabs. The two columns 34 and 36 are spaced apart from one another so that they cooperatively define a top opening 38 in the top flux return member. Columns 34 and 36 lie on opposite sides of the full height slab 20 of the innermost layer in side wall 12 and lie on opposite sides of the corresponding full height slab of wall 14. Columns 34 and 36 rest on the top ends of the partial height slabs 26 and 24 (FIG. 4) and similarly rest on partial height slabs of wall 14. The bottom flux return member 32 includes a similar pair of columns 40 and 42 (FIGS. 3 and 4) defining a similar opening 44 in the bottom flux return member. The side walls and the flux return members thus form a rectilinear box, with the top flux return member 30 constituting the top wall of the box, the bottom flux return member 32 constituting the bottom wall of the box and the side walls 12 and 14 forming the side walls of the box. The box-like frame defines a front patient opening 48 on one side of the frame visible in FIG. 1 and a similar rear patient entry opening 50 on the opposite side of the frame.

In the particular embodiment illustrated, each of the columns 34, 36, 40 and 42 constituting the flux return structures is about 10 feet long, about 2 feet wide (in the horizontal direction) and about 16 inches in the vertical direction. Each side wall is almost 11 feet high and about 7 feet wide. The aggregate thickness of each side wall, including both layers of slabs is about 16 inches. The front and rear patient entry openings 48 and 50 are about 8 feet high by 9 feet wide. The top and bottom openings 38 and 40 are about 3 feet wide and 9 feet long; the top and bottom openings, and extend through the full span of the flux return structures between the inner faces of the side walls. These dimensions are only exemplary. However, the height of each entry opening, and the vertical clearance between the flux return structures, should be greater than the height of an average person, desirably more than about 7 feet and preferably about 8 feet or more. Also, the top and bottom openings desirably have dimensions sufficient to accommodate at least the head or feet of a patient while the patient is positioned on the patient support. The smallest horizontal dimension of each such opening preferably is at least 18 inches, and more preferably at least about 2 feet.

The frame is provided with ferromagnetic reinforcements 52 at each corner. Additional ferromagnetic plates 54 extend from each reinforcement 52 along the top and bottom flux return structures.

Figure 2:
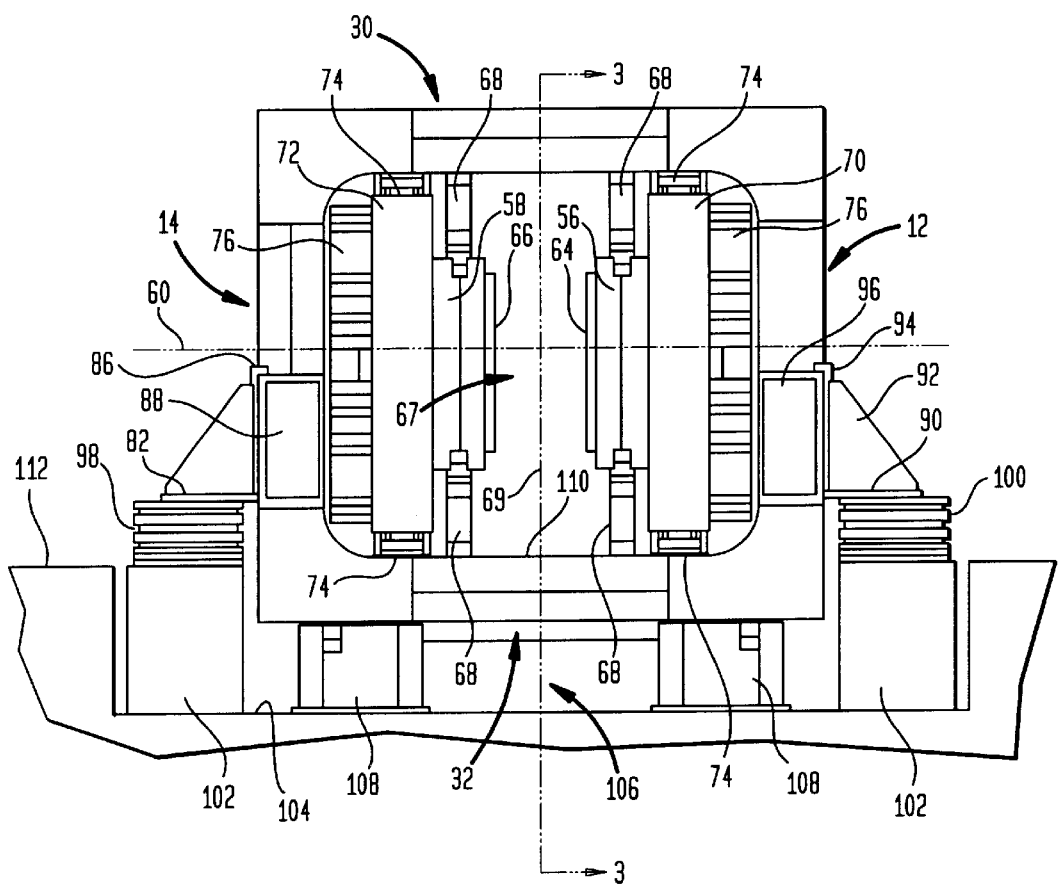
FIG. 2 is a front elevational view of the magnet structure depicted in FIG. 1.

A right side pole 56 extends from the right side wall 12 towards the left side wall 14, and a left pole 58 extends inwardly from left side wall 14 towards left side wall 12. Poles 56 and 58 are generally cylindrical and are coaxial with one another on a common horizontal polar axis 60. Polar axis 60 is disposed midway between the top and bottom flux return members 30 and 32. As best seen in FIG. 4, pole 56 is formed by a series of stacked ferromagnetic metal disks 62 and a pole cap 64 defining the face of the pole remote from the right side wall. Disks 62 may be formed from the same ferromagnetic material as the remainder of the frame. Pole cap 64 desirably is formed from a material which tends to suppress eddy currents during operation of the apparatus. For example, the pole cap may include a ferrite or other electrically resistive ferromagnetic material or may include sheets or laminae of a ferromagnetic material having low electrical resistivity. Suitable pole face designs for suppressing eddy currents are disclosed, for example, in commonly assigned U.S. Pat. Nos. 5,124,651, 5,592,089 and 5,061,897, the disclosures of which are incorporated by reference herein. Left pole 58 is identical to the right pole and has a similar pole cap defining a left pole face 66 (FIG. 2). In the illustrated embodiment, the pole faces 64 and 66 desirably are about 52 inches in diameter. The pole faces typically are shaped or profiled so as to maximize field uniformity. For example, each pole face may have an axially projecting ridge adjacent it periphery.

Pole cradles 68 formed from a non-ferromagnetic material extend vertically between poles 56 and 58 and the flux return members or walls 30 and 32. These pole cradles physically support the ends of the poles remote from side walls 12 and 14.

Poles 56 and 58 are surrounded by electromagnet coil assembly 70 and 72, respectively. In the particular embodiment illustrated these coils are resistive coils. The outer jackets of the poles are depicted; the internal windings are omitted for clarity of illustration. In the illustrated embodiment, each coil assembly carries about 181,200 ampere-turns. Coil cradles 74, formed from a non-ferromagnetic material extend between the outer jackets of the coils and the flux return members 30 and 32. Coil pedestals 76, also formed from a non-ferromagnetic material, are provided between coil 70 and right side wall 12 and between coil 72 and left side wall 14. The coils are omitted in FIG. 1 for clarity of illustration. The coils are retained on the coil pedestals by non-ferromagnetic coil support plates 80 (FIG. 3) on the side of each coil remote from the coil support plates.

The ferromagnetic elements of the frame desirably are formed from low-carbon steel such as 1001 or 1006 steel. The non-ferromagnetic elements desirably are formed from aluminum.

Figure 3:
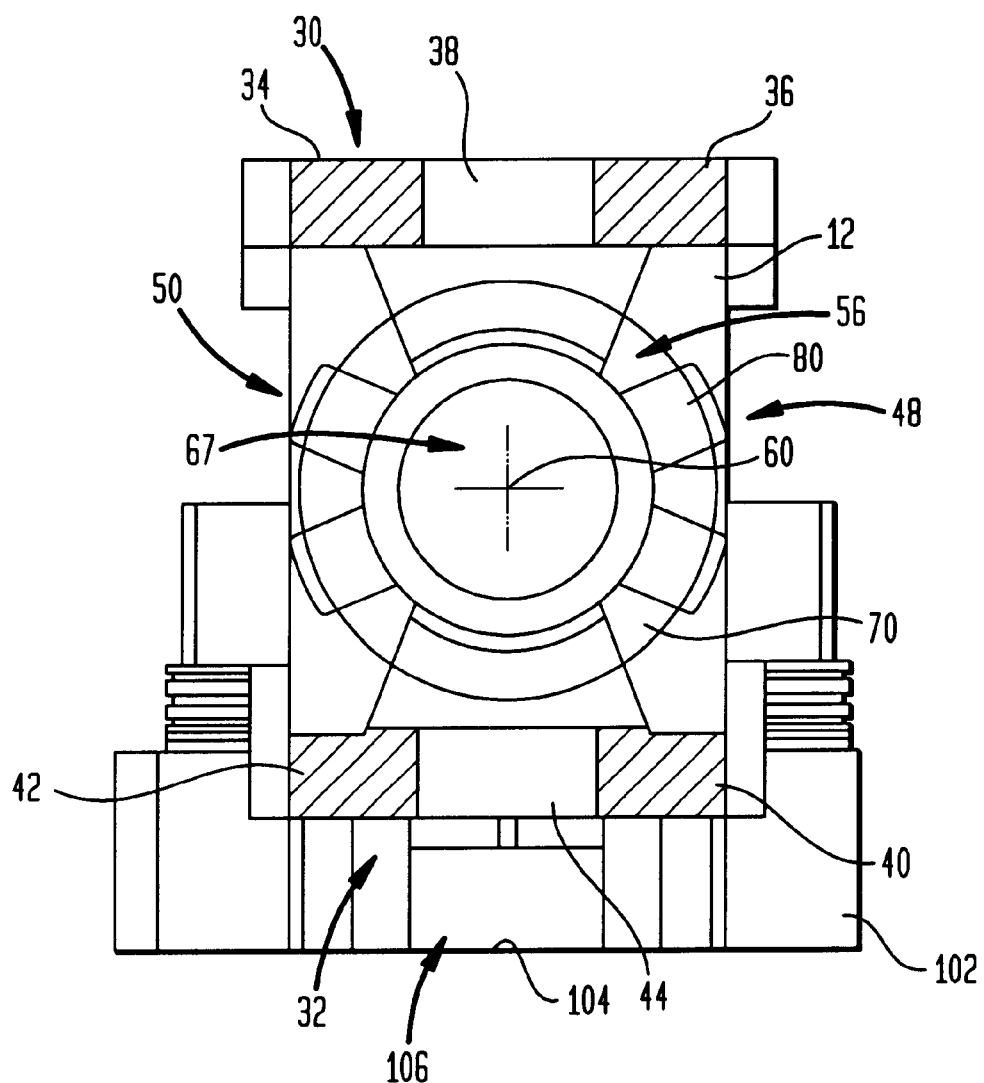
FIG. 3 is a sectional view taken along line 3—3 in FIG. 2.

The polar axis 60 is aligned with the openings 38 and 44 in the top and bottom flux return members (FIG. 3). The pole faces 64 and 66 confront one another and cooperatively define a patient-receiving space 67 between them. The patient-receiving space encompasses the vertical medial plane 69 of the frame, midway between the side walls 12 and 14, and is centered on polar axis 60.

A left side bracket 82 extends along the outer face of left side wall 84. The left side bracket is a generally L-shaped member with a vertical portion abutting the side wall and a horizontal portion projecting outwardly from the side wall. Angle braces 84 are provided within the L-shaped member. The upper edge of the L-shaped left bracket 84 is engaged with a solid key 86 which in turn is engaged in a slot in the left side wall 14. A pair of box-like members, referred to herein as "anti-twist members" 88 project forwardly and rearwardly from the left side wall. These anti-twist members are attached to the edge face of the left side wall and to the left gusset 82. The right side wall is provided with a similar arrangement including a right bracket 90, triangular bracing 92 within the right bracket and a key 94 engaged between the top edge of the right bracket 90 and the right side wall 12. Box-like anti-twist members 96 are also provided on the edges of the right side wall.

The magnet structure further includes a left side set of vibration isolators 98 disposed beneath the left side bracket 82 and a right side set of vibration isolators 100 disposed beneath the right side bracket 90. The vibration isolators include flexible structure capable of supporting the weight of the frame. In the particular embodiment illustrated, each vibration isolator includes a stack of inflatable bladders. The vibration isolators are supported by a foundation 102, which includes a pair of spaced-apart blocks resting on an underlying base surface 104. The foundation projects upwardly from the base structure so that the foundation and the vibration isolators maintain the frame above the base surface and maintain the bottom flux return structure 32 above the base surface 104. Thus, there is a space 106 beneath the bottom flux return member in alignment with the opening 44 (FIG. 3) in the bottom flux return member. Four support blocks 108 are positioned on the base surface 104. In the normal operating condition of the apparatus, the tops of the support blocks 108 are lie below the bottom surface of the bottom flux return member. These blocks 108 are arranged to support the lower flux return member 32 and the hence to support the entire frame during construction and during servicing of the vibration isolators 100 and 98.

Figure 5:
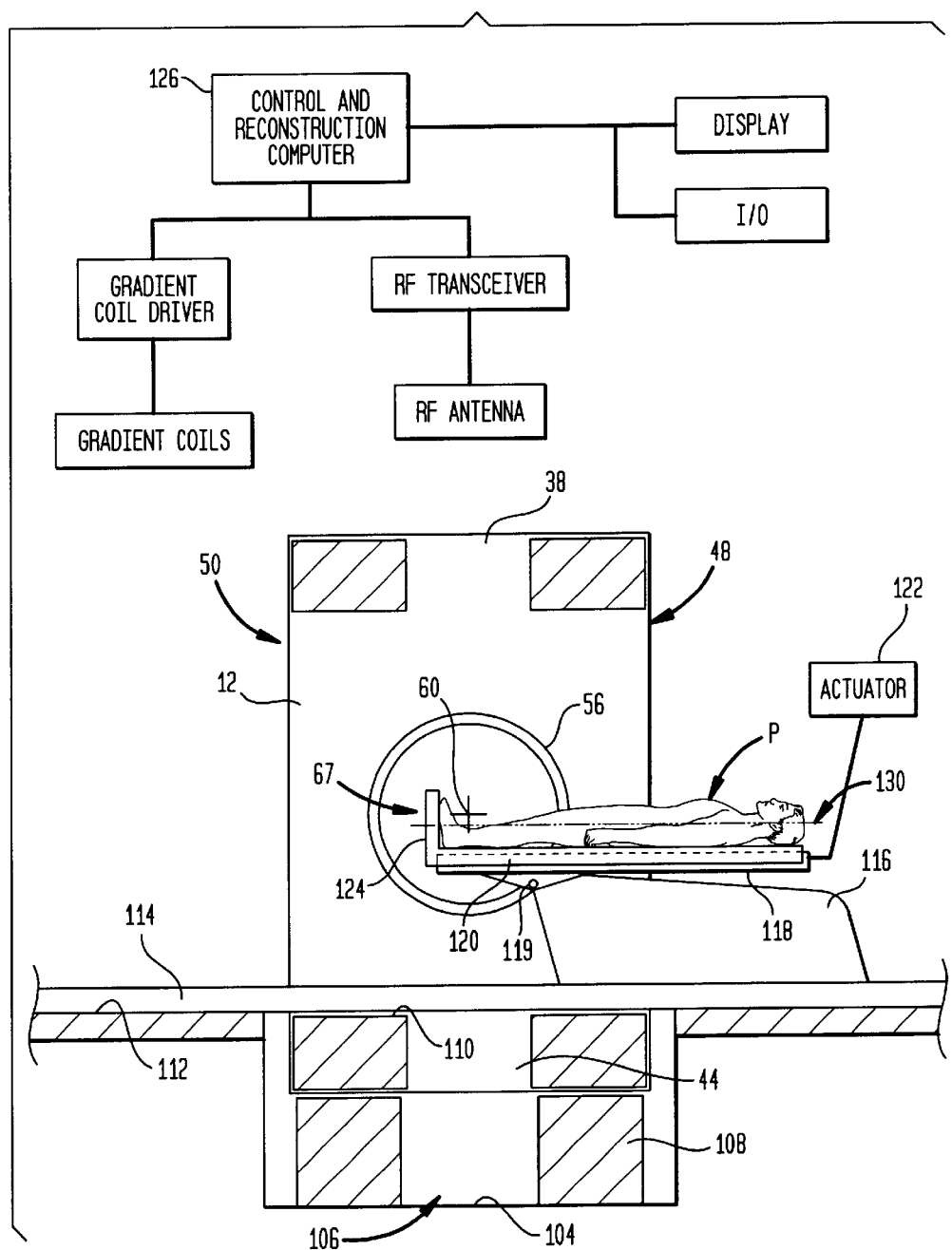
FIG. 5 is a diagrammatic sectional view of the structure shown in FIGS. 1–4 in conjunction with additional apparatus elements and a patient.

Lower flux return member 32 defines an upwardly facing floor surface 110. The building in which the apparatus is employed defines a floor surface 112 (FIGS. 2 and 5) at about the same height as floor surface 110. As best seen in FIG. 5, a simplified cross-sectional view of the apparatus, the floor surface 112 of the building is adjacent to the floor surface 110 at the patient entry openings 48 and 50 so as to form a substantially continuous, level floor. A set of rails 114 extends through the patient entry opening 48 in the front of the apparatus and through patient entry opening 50 at the rear of the apparatus. Rails extend across the floor surface 110 defined by the lower flux return member and across the floor surface 112 defined by the surrounding building structure. A carriage 116 is mounted on the rails so that the carriage can be moved along the rails, into and out of the frame through either patient entry opening.

A patient support assembly including an elevator having an elongated elevator frame 118 and a patient support 120 is also provided. The patient support is slideable along the elevator frame (to the left and right as seen in FIG. 5). An actuator 122 schematically indicated in FIG. 5 is connected between the elevator frame 118 and the patient support 120. The actuator may include essentially any device capable of moving the patient support relative to the frame as, for example, pneumatic cylinders and hydraulic cylinders, and screws, cables or other motion-transmitting elements linked to electric or fluid driven motors. Where electric motors are employed, the same should be electrically and magnetically shielded. Also, those elements of the patient support assembly, including the patient support 120, elevator 120 and actuator 122, which will be positioned in the patient receiving space of the apparatus during actual MRI scanning operations, desirably are formed from non-magnetic materials. Where actuator 122 includes one or more electric motors or other elements which have ferromagnetic components, these elements can be positioned on a part of carriage 116 which is disposed outside of the patient-receiving space during use of the apparatus.

Patient support 120 preferably has a foot rest 124 at a lower end of the support. The patient support may also include conventional devices such as straps and cushions for retaining the patient in position on the support and for providing patient comfort during the procedure. Elevator frame 118 is mounted to the carriage 116 for pivoting movement about a pivot axis 119. Pivot axis 119 extends horizontally and hence is parallel to the polar axis 60. The carriage may further include devices (not shown) for raising or lowering pivot axis 119 and hence raising and lowering the elevator frame 118 and patient support 110 relative to the carriage.

The apparatus is used in conjunction with a control and reconstruction computer 126 linked to a display apparatus and input/output or "I/O" devices for actuating the computer. The control and reconstruction computer 126 is also linked to a set of gradient coils through a gradient coil driver adapted to supply appropriate currents to the gradient coils responsive to commands from the control and reconstruction computer. The control and reconstruction computer is also linked to a radio frequency transceiver which in turn is connected to one or more RF antennas. These elements of the apparatus may be entirely conventional. In the normal manner, the gradient coils are disposed within the apparatus. Typically, the gradient coils are mounted in proximity to the faces of the poles. The RF antenna may be mounted on the magnet frame; mounted on the patient support structure or even attached by the patient.

In an imaging method according to one embodiment of the invention, a patient P is positioned on patient support 120 in a generally horizontal position, i.e. with the patient's axis of elongation or head to toe axis 130 horizontal. For example, the patient may be prone or supine or may be lying on his or her side. Desirably, the patient is positioned on the patient support while the carriage 116 is outside of frame 10. Thus, the carriage 116 may be moved to a retracted position remote from the magnet frame and the patient may be loaded onto the magnet frame while the carriage is in this remote position. The patient may be imaged in this horizontal position. Any portion of the patient may be aligned with the polar axis 60 by moving the carriage along the rails, by actuating the elevator to move the patient support relative to frame 118, or both.

Figure 6:
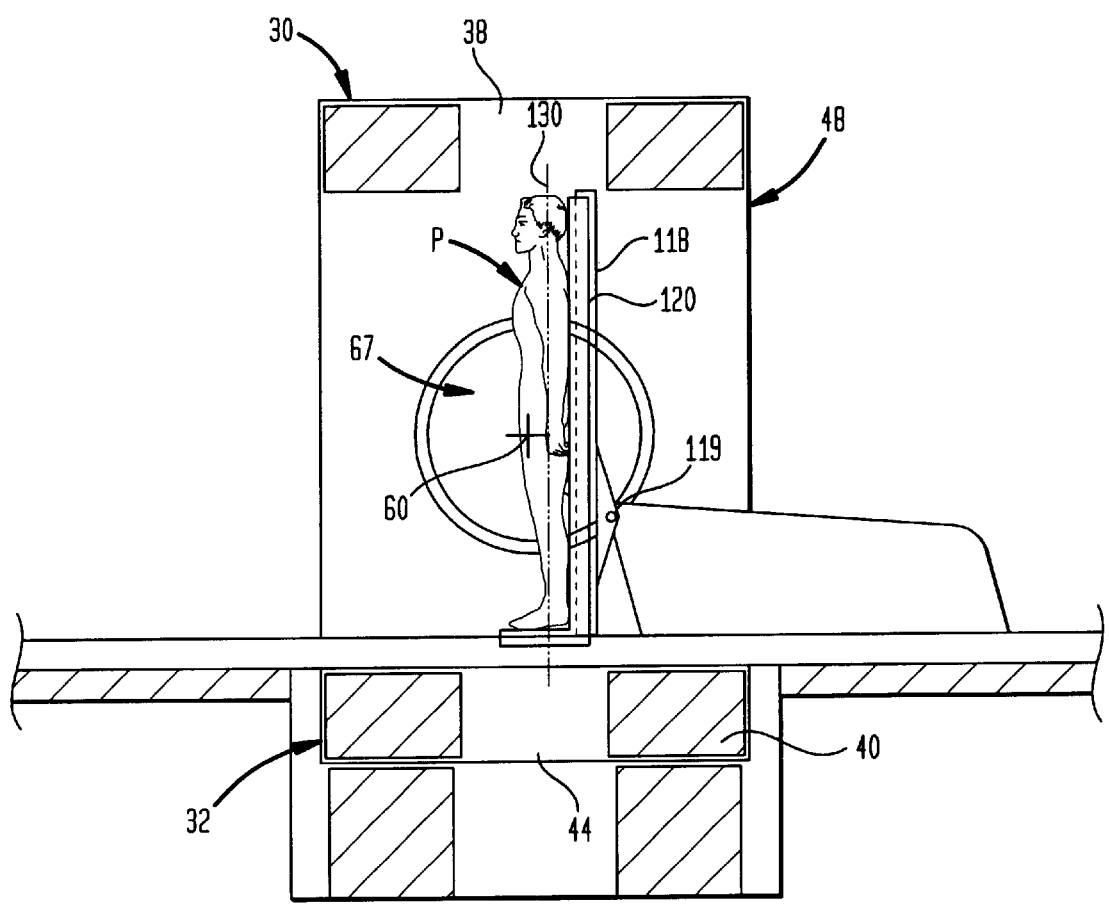
FIGS. 6, 7 and 8 are views similar to FIG. 5 but depicting the apparatus during other phases of operation.
Figure 7:
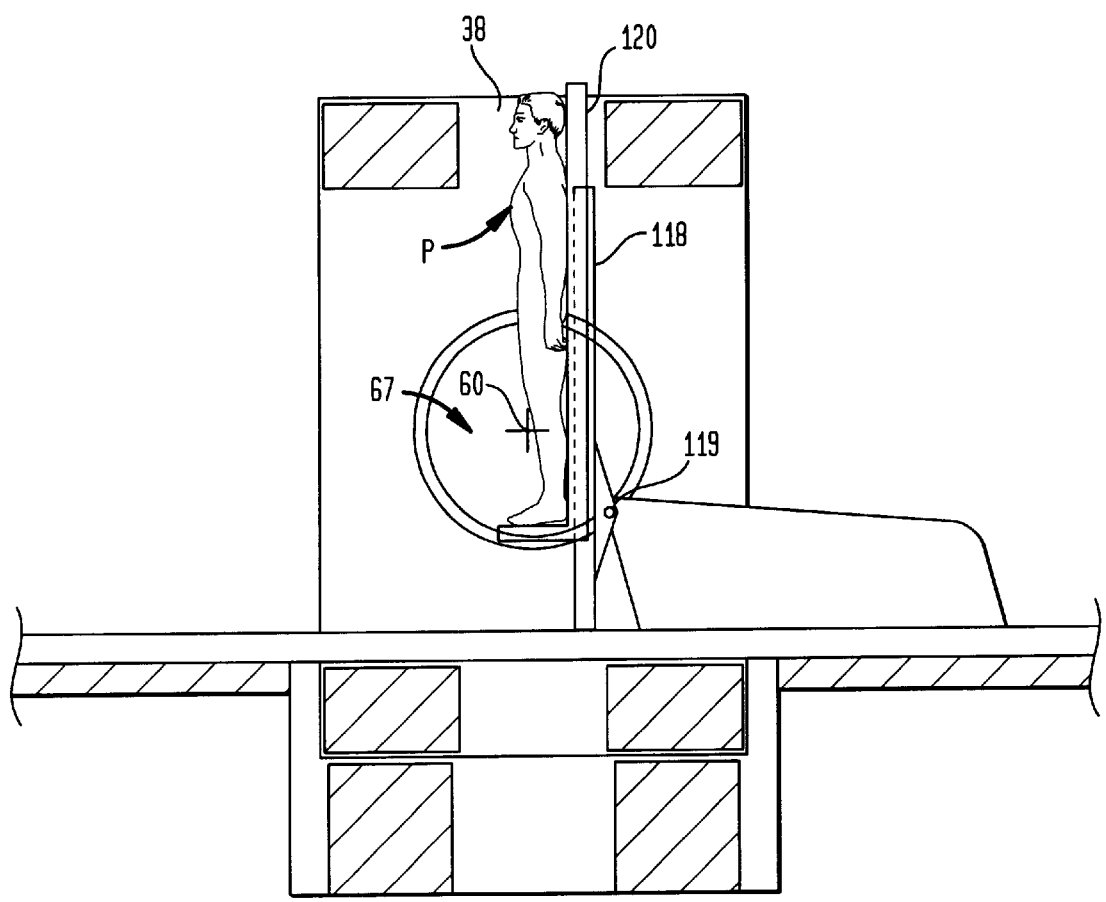

Alternatively, as shown in FIG. 6, the elevator 118 and patient support 120 may be pivoted about pivot axis 119 so as to move the patient a standing position with the long axis 130 of the patient substantially vertical. In this condition, the patient support 120 and the patient P are aligned with the top opening 38 in the top flux return structure 30 and with the bottom opening 40 in the bottom flux return structure. A portion of the patient is disposed in the patient-receiving space 67 between the poles of the magnet frame. In the particular condition illustrated in FIG. 6, the lower torso of the patient is aligned with the polar axis 60, and parts of the body including the lower torso can be imaged. However, the patient support 120 can be moved by the actuator 122 (FIG. 5) relative to the elevator frame 118 so as to move the patient vertically and bring any desired portion of the patient into aligned with the polar axis 60. For example, as seen in FIG. 7, the patient support has been raised to a position in which a part of the patient support 120 and the patient's head protrude upwardly into the top opening 38. In this condition, the patient's legs are disposed within the patient receiving space, near the polar axis 60. This allows imaging of the legs while the patient remains in a standing condition.

Figure 8:
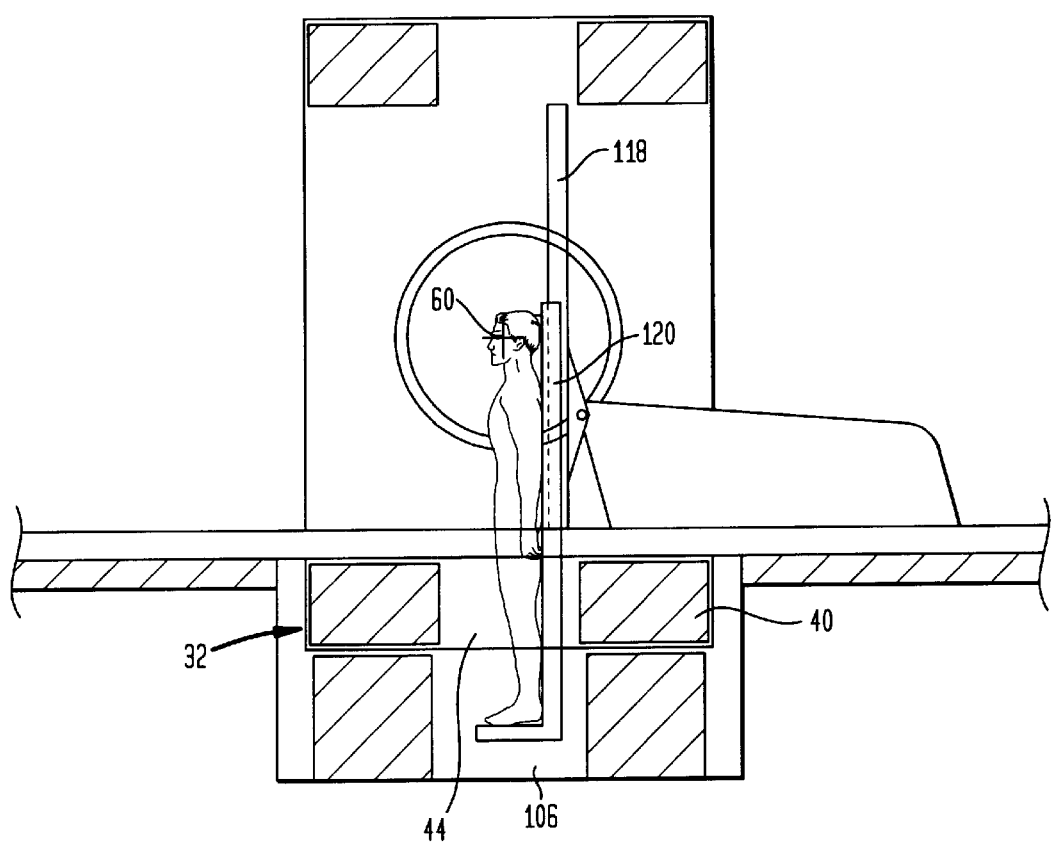

Patient support 120 can be lowered relative to the elevator frame and hence relative to the magnet frame to the position shown in FIG. 8 in which a portion of the patient support and the patient's feet protrude into the lower opening 40 in the bottom flux return structure and also protrude below the flux return structure into the space 106 beneath the bottom flux return structure. In this condition, the patient's head is aligned with the polar axis of the apparatus.

The apparatus thus allows imaging of essentially any part of the patient's body while the patient is in a standing position, with his long axis vertical or while the patient is in a horizontal position. The apparatus discussed above also can image a patient while the patient is in an intermediate position between horizontal and vertical orientations. For example, by tilting the patient support 120 and elevator frame 118 to a position intermediate between the position depicted in FIG. 5 and the position depicted in FIG. 6, the patient can be placed into a reverse Trendlenberg position, with his head elevated slightly relative to his feet and with his long axis 130 at an oblique angle to the horizontal and vertical directions. If the patient is initially positioned on the support with his head adjacent foot rest 124, a similar pivoting motion will place the patient into a conventional Trendlenberg position, with his head depressed relative to his feet. With the other frame and patient support in this oblique position, the actuator 122 (FIG. 5) can be used to move the patient support along the elevator frame and thus align different portions of the patient's body with the patient receiving space 67 and polar axis 60. Carriage 116 can be moved along rails 114 in conjunction with movement of the patient support 120 on frame 118. Thus, essentially any portion of the subject's body can be placed within the patient receiving space 67, in alignment with the poles and imaged while the patient is in essentially any position.

The ability to image patients in different positions is particularly helpful where orientation of the body will influence the structure or function of the body part to be imaged. For example, an image of a skeletal structure can be captured while the structure is bearing the patient's normal weight in a standing posture. Also, as described in greater detail in U.S. provisional patent application No. 60/167,395 filed Nov. 24, 1999, the disclosure of which is hereby incorporated by reference herein, the dynamics of fluid flow in the body also vary with position of the patient. An image of the fluid containing structures of the body, as, for example, an angiogram of the coronary arteries captured while the patient is in an erect position as, for example, standing will provide additional information, beyond that which can be obtained from a similar image captured while the patient is supine. Apparatus and methods according to the present invention can be utilized in capturing angiograms, images of structures containing the cerebral spinal fluid and other images of fluid containing structures in the body.

The functions discussed above are provided in a magnet frame which has inherently good magnetic field uniformity. Moreover, the magnet can be erected in the field at reasonable cost, and provides a relatively non-claustrophobic experience for the patient. To facilitate the fabrication of the magnet, some parts of the magnet frame depicted as solid elements herein can be formed as a series of sheets which can be stacked and bolted or otherwise connected together in the field. The use of laminates in a magnet frame is discussed in greater detail in the copending, commonly assigned United States provisional patent application entitled MRI Magnet Frame With Laminated Carbon Steel, filed on or about Nov. 21, 2000 and naming Luciano B. Bonnani as the inventor, the disclosure of which is hereby incorporated by reference herein.

Numerous variations and combinations of the features discussed above can be utilized without departing from the present invention as defined by the claims. In one such variation, the poles are not circular cylinders as discussed above, but instead are elongated in the vertical direction. For example, the poles may be generally elliptical, with their major axes extending in the vertical direction. This provides a vertically elongated patient receiving space and elongated imaging volume. Also, it is not essential to position the patient on the support while the support is in a horizontal orientation. The support may be in the vertical orientation as seen in FIG. 6 or in an oblique position when the patient is placed on the support. Also, the support need not incorporate a bed. For example, if the patient is to be imaged in a seated position, the support may include a seat. The apparatus typically includes shrouds and concealments structures for hiding the operative elements of the apparatus from view by the patient. For example, the floor 110 defined by the lower flux return structure may be covered by a conventional floor covering material. It is not essential to use a carriage arrangement as discussed above in loading the patient within the apparatus. Lower opening 44 may be covered by a floor panel (not shown) adapted to support the weight of the patient in which case the patient can walk into the apparatus or be positioned in the apparatus on a chair, litter or other mobile support. Such a panel can be raised or lowered by an elevator mechanism to provide for imaging of different portions of the patient's body. For example, the elevator mechanism used to drive a movable floor panel may be mounted in the space 106 beneath the lower flux return member. Further, the flux return structures need not have flat surfaces. Acceptable, but less preferred, flux return structures can incorporate cylindrical or elliptical columns. A non-ferromagnetic false floor can be mounted on the columns of the lower flux return structure. Also, the floor structure 112 disposed outside of the patient entry openings 48 and 50 need not be flat and need not be part of the building structure. Thus, in a less-preferred embodiment, the floor structure may include a pair of ramps (not shown) sloping upwardly to meet the floor structure 110 within the frame.

The apparatus can be used to image a large number of patients in sequence. Thus, plural carriages, patient supports and elevators as discussed above can be provided. One carriage can be loaded with a patient and adjusted to the desired orientation while a patient carried by the other carriage is being imaged. Also, the preferred dimensions and materials discussed hereinabove are merely exemplary. These dimensions and materials can be varied.

As these and other variations and combinations of the features discussed above can be utilized without departing from the present invention, the foregoing description of the preferred embodiment should be taken by way of illustration rather than by way of limitation of the invention as defined by the claims.

What is claimed is:

1. MRI apparatus comprising:
   (a) a magnet frame including two vertically-extending side walls and a pair of ferromagnetic poles projecting inwardly along a polar axis from each said side wall towards the other said side wall, a top flux return structure extending between said side walls above said poles and a bottom flux return structure extending between said side walls below said poles, said frame defining a patient receiving space within said interior space between said poles,
   (b) a floor structure in proximity to bottom flux return structure so that a patient may enter said patient-receiving space by moving across said floor structure and entering into said frame on or above said bottom flux return structure; and
   (c) a source of magnetic flux for providing magnetic flux in said patient-receiving space through said poles.

2. An apparatus as claimed in claim 1, wherein said top flux return structure has an opening therein aligned with said patient-receiving space, said opening being of sufficient size to accommodate a patient.

3. An apparatus as claimed in claim 2, wherein said bottom flux return structure has an opening therein aligned with said patient-receiving space.

4. An apparatus as claimed in claim 3 wherein said opening in said bottom flux return structure is of sufficient size to accommodate a patient.

5. An apparatus as claimed in claim 4, further comprising an elevator for raising and lowering a patient relative to said frame.

6. An apparatus as claimed in claim 5 further comprising a carriage, said elevator being mounted to said carriage, the apparatus further comprising a patient support mounted to said elevator, said elevator being and operative to raise and lower said patient support relative to said carriage, said carriage being movable between a retracted position in which said patient support is outside of the frame and an operative position in which said patient support is aligned with said patient-receiving space.

7. An apparatus as claimed in claim 6 wherein said patient support includes an elongated bed, said elevator and said patient support being constructed and arranged so that said bed can be pivoted between a substantially horizontal position and a substantially vertical position.

8. An apparatus as claimed in claim 7 wherein said elevator includes an elongated elevator frame mounted to said carriage for pivoting movement about a horizontal pivot axis, said elevator being arranged to move the bed along the elevator frame in its direction of elongation.

9. An apparatus as claimed in claim 1, wherein said source of magnetic flux includes electromagnet coils surrounding said pole stems.

10. An apparatus as claimed in claim 9, further comprising non-ferromagnetic coil pedestals disposed between said coils and said side walls.

11. An apparatus as claimed in claim 9, further comprising non-ferromagnetic coil cradles associated with each said coil, the coil cradles associated with each said coil including a top coil cradle disposed between the coil and said top flux return structure and a bottom coil cradle disposed between the coil and said bottom flux return structure.

12. An apparatus as claimed in claim 1, wherein said top flux return structure, bottom flux return structure and side walls define a pair of patient entry openings, whereby a patient can enter into said frame or exit from said frame by passing through either said pair of patient entry openings.

13. An apparatus as claimed in claim 1 wherein said bottom flux return structure is a bottom wall defining a substantially flat, horizontal upper surface.

14. An apparatus as claimed in claim 13 wherein said upper surface of said bottom wall is aligned with said floor.

15. An apparatus as claimed in claim 14 wherein said floor is substantially horizontal.

16. An apparatus as claimed in claim 1 further comprising a support structure and a plurality of vibration isolators holding said frame on or above said support structure.

17. An apparatus as claimed in claim 16, wherein said plurality of vibration isolators include cushions filled with a fluid.

18. An apparatus as claimed in claim 16, further comprising one or more blocks underneath said frame, said vibration isolators holding said frame above said blocks so that said blocks do not normally bear the weight of said frame, but said blocks can bear the weight when said vibration isolators are being serviced.

19. MRI apparatus comprising:
(a) a magnet frame including two vertically-extending side walls and a pair of ferromagnetic poles projecting inwardly along a polar axis from each said side wall towards the other said side wall, a top flux return structure extending between said side walls above said poles and a bottom flux return structure extending between said side walls below said poles, said frame defining an interior space between said side walls and between said flux return structures and a patient receiving space within said interior space between said poles, said frame also defining at least one patient entry opening allowing movement of a patient in a substantially horizontal direction into and out of the interior space, at least one of said flux return structures defining an opening above or below said patient receiving space;
(b) an elevator for raising and lowering a patient while said patient is positioned in the interior space so as to position a first portion of the patient within said patient receiving space; and
(c) a source of magnetic flux for providing magnetic flux in said patient-receiving space through said poles.

20. Apparatus as claimed in claim 19 further comprising a patient support capable of maintaining a patient in said interior space in a substantially vertical orientation, said elevator being constructed and arranged to raise or lower the patient while the patient is disposed in said vertical orientation.

21. An apparatus as claimed in claim 20 further comprising a carriage, said elevator being mounted to said carriage, the apparatus further comprising a patient support mounted to said elevator, said elevator being and operative to raise and lower said patient support relative to said carriage, said carriage being movable between a retracted position in which said patient support is outside of the frame and an operative position in which said patient support is aligned with said patient-receiving space.

22. An apparatus as claimed in claim 21 wherein said patient support includes an elongated bed, said elevator and said patient support being constructed and arranged so that said bed can be pivoted between a substantially horizontal position and a substantially vertical position.

23. An apparatus as claimed in claim 22 wherein said elevator includes an elongated elevator frame mounted to said carriage for pivoting movement about a horizontal pivot axis, said elevator being arranged to move the bed along the elevator frame in its direction of elongation.

24. MRI apparatus comprising:
(a) a magnet frame including two vertically-extending side walls and a pair of ferromagnetic poles projecting inwardly along a polar axis from each said side wall towards the other said side wall, a top flux return structure extending between said side walls above said poles and a bottom flux return structure extending between said side walls below said poles, said frame defining an interior space between said side walls and between said flux return structures and a patient receiving space within said interior space between said poles, said frame also defining at least one patient entry opening allowing movement of a patient in a substantially horizontal direction into and out of the interior space, at least one of said flux return structures defining an opening above or below said patient receiving space;
(b) a patient support capable of maintaining a patient in said interior space in a substantially vertical orientation;and
(c) a source of magnetic flux for providing magnetic flux in said patient-receiving space through said poles.

25. A method of magnetic resonance imaging comprising the steps of:
a. Positioning a patient within a magnet having a frame with vertically-extensive side walls, top and bottom flux return structures extending between said side walls and poles projecting along a horizontal polar axis from each said side wall toward the other said side wall and defining a patient receiving space therebetween, said positioning step including allowing the patient to enter into the frame through an entry opening defined by said side walls and said flux return structures so that the patient passes into the frame above the bottom flux return structure and below the top flux return structure; and
b. conducting magnetic resonance imaging of said patient using said magnet.

26. A method as claimed in claim 25, wherein said step of positioning the patient includes orienting the patient substantially vertically within the frame and raising or lowering the patient relative to the frame so that one portion of the patient extends into an opening in one of said flux return structures and another portion of the patient is disposed in said patient-receiving space.

27. A method as claimed in claim 26 wherein said step of positioning the patient includes advancing the patient into the frame on a support carried by a carriage, said step of raising or lowering the patient including raising or lowering the support relative to the carriage.

28. A method as claimed in claim 27 wherein said step of advancing the patient is performed while the patient is in a substantially horizontal orientation, the step of positioning the patient including pivoting the support to bring the patient to said substantially vertical orientation while the patient is at least partially disposed within the frame of the magnet.

29. A method as claimed in claim 26 wherein said raising or lowering step includes raising the patient so that the patient's head protrudes into an opening in the top flux return structure.

30. A method as claimed in claim 26 wherein said raising or lowering step includes lowering the patient so that the patient's feet protrude into an opening in the bottom flux return structure.

31. A method as claimed in claim 25, wherein said step of positioning the patient includes allowing the patient to walk into the interior of the frame.

* * * * *

UNITED STATES PATENT AND TRADEMARK OFFICE
CERTIFICATE OF CORRECTION

PATENT NO. : 6,677,753 B1  
DATED : January 13, 2004  
INVENTOR(S) : Gordon T. Danby et al.

Page 1 of 1

It is certified that error appears in the above-identified patent and that said Letters Patent is hereby corrected as shown below:

<u>Column 2,</u>  
Line 65, "walls the poles" should read -- walls of the poles --.

<u>Column 5,</u>  
Line 5, "38 and 40" should read -- 38 and 44 --.

<u>Column 8,</u>  
Line 5, "patient a standing" should read -- patient to a standing --.  
Lines 9 and 28, "opening 40" should read -- opening 44 --.

<u>Column 10,</u>  
Line 17, "two vertically" should read -- two ferromagnetic vertically --.  
Line 26, "to bottom" should read -- to said bottom --.  
Line 49, "being and operative" should read -- being operative --.

<u>Column 11,</u>  
Line 65, "being and operative" should read -- being operative --.

Signed and Sealed this

Twentieth Day of April, 2004

JON W. DUDAS  
*Acting Director of the United States Patent and Trademark Office*